United States Patent [19]

Harshe et al.

[11] Patent Number: 4,830,022

[45] Date of Patent: May 16, 1989

[54] ANIMAL MONITORING SYSTEM

[75] Inventors: Bruce L. Harshe, Jackson; Robert H. Ashton, Watervliet, both of Mich.

[73] Assignee: Medical Engineering and Development, Inc., Jackson, Mich.

[21] Appl. No.: 78,090

[22] Filed: Jul. 27, 1987

[51] Int. Cl.$^4$ .............................................. A61B 5/08
[52] U.S. Cl. .................................. 128/724; 73/204.23
[58] Field of Search ....................... 128/724, 725, 671; 73/204.11, 204.23, 204.25, 204.17

[56] References Cited

U.S. PATENT DOCUMENTS

| | | | |
|---|---|---|---|
| 2,904,033 | 9/1959 | Shane | 128/716 |
| 3,232,288 | 2/1966 | Krobath | 128/724 |
| 3,513,832 | 5/1970 | Klemm et al. | 128/671 |
| 3,530,850 | 9/1970 | Edwards, Jr. | 128/716 |
| 3,645,133 | 2/1972 | Simeth et al. | 128/725 X |
| 3,817,238 | 6/1974 | Matson | 128/716 |
| 3,990,435 | 11/1976 | Murphy | 128/716 |
| 4,363,238 | 12/1982 | William | 128/724 |
| 4,417,589 | 11/1983 | Favaloro | 128/716 |
| 4,522,204 | 6/1985 | Kurahashi et al. | 128/719 |

OTHER PUBLICATIONS

Chess et al, "Apnoea Monitor . . . Animals", Med. & Biol. Eng., vol. 14, No. 1, pp. 97-100, Jan. 1976.
Graystone, "A Self-Centering Respiration Monitor . . . ", IEEE Trans. Biomed. Eng., 1971, pp. 382-383.
Sekey et al, "Bidirectional Subminiature Thermistor . . . ", Biomed. Med. Dev. Art Org., 9(1), 73-90 (1981).

Primary Examiner—Lee S. Cohen
Attorney, Agent, or Firm—Beaman & Beaman

[57] ABSTRACT

A system for monitoring animal body functions by analyzing the condition of the gas being breathed. A breathing tube, usually constituting a portion of anesthesia apparatus, contains sensing means in the form of a thermobead whose electric characteristics vary in accordance with temperature variations as heat is exchanged between the thermobead and the respiratory gas. Electronic analysis of the thermobead characteristics permits animal body functions such as breathing rate, breathing volume, animal body temperature and the like to be determined. Digital displays, recorders and alarms may be activated by the thermobead output.

4 Claims, 1 Drawing Sheet

ANIMAL MONITORING SYSTEM

BACKGROUND OF THE INVENTION

In the animal husbandry art it is common to use anesthesia to calm and immobilize animals during surgery or for other reasons. During the duration that the animal is under anesthesia it is highly desirable to monitor critical body functions, such as breathing and body temperature, to insure that the animal is stable and is receiving the proper dosage.

The rate of breathing, and the volume of gas being breathed, are significant factors in analyzing the condition of an animal while under anesthesia, and various devices have been proposed for monitoring breathing cycles, for instance, microphone systems are commonly used to give an indication of animal breathing cycles. Respiratory monitors for animals are shown in U.S. Pat. Nos. 3,817,238 and 4,417,589, and respiratory analyzing apparatus suitable for humans or usable with animals are shown in U.S. Pat. Nos. 2,904,033; 3,530,850; 3,990,435 and 4,522,204.

Known respiratory monitors, while capable of sensing and amplifying breathing sounds, do not give an accurate indication of the depth of breathing, the volume of gas being inhaled, variations in breathing characteristics during inhalation or exhalation, and do not provide the degree of sensitivity which is highly desirable.

It is an object of the invention to provide an animal monitoring system for analyzing animal body functions through the characteristics and variations occurring in the respiratory system.

A further object of the invention is to provide an animal monitoring system associated with the gas being breathed wherein the volume of the breathed gas, the velocity of the gas during the breathing cycle, and the temperature thereof, may all be accurately electronically sensed to permit instantaneous readout and indication.

An additional object of the invention is to provide an animal monitoring system sensing the animal breathing cycle wherein an amplified audio frequency is generated whose amplitude or frequency accurately simulates normal breathing sounds.

Yet a further object of the invention is to provide an animal monitoring system using a thermobead transducer within a breathing tube wherein the transducer generates a known temperature and the rate of heat exchange between the thermobead and the breath gas modifies an electronic signal capable of indicating the rate, intensity and volume of breathing characteristics, and may also be used to indicate body temperature.

In the practice of the invention a breathing tube is utilized through which the animal's breath passes. The tube may be associated with an induction mask or an endotracheal tube. Usually, the breathing tube will be incorporated into an anesthetic loop and a sensing transducer within the breathing tube produces an electronic signal indicating the condition of the gas being breathed.

The transducer comprises a very small self-heated thermobead including an electronic circuit which maintains the thermobead at approximately 200 degrees Centigrade. The thermobead is located within the breathing passage tube in direct exposure to the gas being breathed by the animal, and as the gas passes over the thermobead, heat exchange takes place tending to cool the bead and thereby modify the electric conducting characteristics of the thermobead. This varying signal is electronically analyzed and amplified for readout indicating and alarm purposes. The resultant signal can be used to generate an amplified audio output and frequency indicating to the veterinarian the exact condition of the breathing cycle. Another thermobead may also be employed to indicate the temperature of the breath, and directly indicate the animal body temperature. The signal operates electronic displays of the digital or analog type, and may also be used to activate alarms when the signal falls below or rises above predetermined limits.

The rate of heat exchange between the thermobead and the gas being breathed is determined by the temperature of the gas and its flow rate. During each cycle of inhalation and exhalation both the gas temperature and its flow rate vary, and the instantaneous variations in the transducer output permit very accurate analyzing and amplification of the breath characteristics. The velocity of breath gas movement can readily be interpolated to indicate the volume of breathing, and likewise, when sensing the temperature of the animal's breath during exhalation the animal's body temperature may be accurately observed.

The animal monitoring system of the invention is relatively economical, requires a minimum of skill on the part of the operator, and is rugged and dependable.

BRIEF DESCRIPTION OF THE DRAWINGS

The aforementioned objects and advantages of the invention will be appreciated from the following description and accompanying drawings wherein.

DESCRIPTION OF THE PREFERRED EMBODIMENTS

Figure 1:
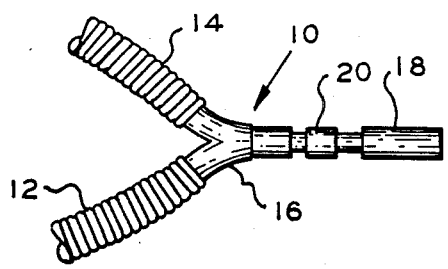
FIG. 1 is a partial, elevational view of a typical animal anesthesic loop illustrating the anesthesic hoses and an endotracheal tube.

The anesthetic apparatus of FIG. 1 as represented at 10 includes a corrugated flexible hose 12 receiving gas from the anesthesic machine, and the similar hose 14 transfers gas from the animal to the anesthesic apparatus. A Y-piece 16 interconnects the ends of the hoses 12 and 14 to the breathing tube 18 which may comprise an endotracheal tube received within the mouth of the animal, or communicating with an induction mask. The transducer 20 in accord with the invention is preferably located between the Y-piece 16 and the tube 18, but it is also possible to locate the transducer 20 within the tubes 12 or 14. It will be appreciated that all of the gas entering the tube 18 will pass through the transducer 20.

Figure 2:
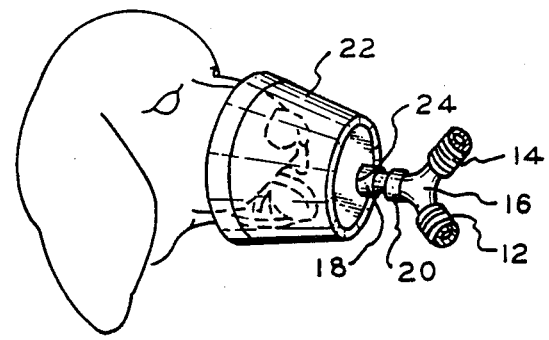
FIG. 2 is an elevational view of a dog having an induction mask located upon its muzzle, and the anesthesic loop of FIG. 1 being associated therein.

With reference to FIG. 2, the tube 18 may communicate with an induction mask 22 positionable over the mouth and nose of an animal, such as the illustrated dog, whereby breathing into the mask causes flow within the tube 18. The tube 18 centrally enters the mask through an opening 24.

Figure 4:
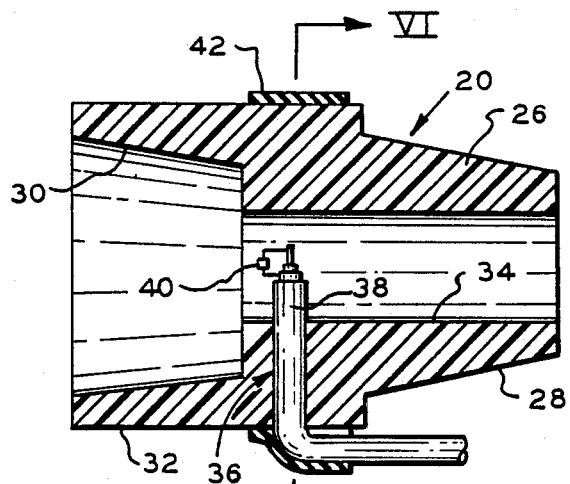
FIG. 4 is an enlarged, diametrical, sectional view of the transducer of the animal monitoring system of the invention.
Figure 3:
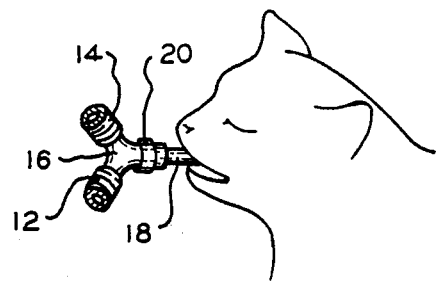
FIG. 3 is an elevational view of an endotracheal tube arrangement incorporating the inventive concepts as employed with a cat.

The general configuration of a typical transducer 20 will be appreciated from FIG. 4. The transducer includes a body 26, preferably formed of a sterilizable material, usually of a synthetic nature, and the transducer includes an exterior conical surface 28 and an interior conical surface 30 whereby the transducer may be readily connected to the Y-piece 16 and tube 18 in a sealed manner. Exteriorly, the body 26 includes a cylindrical surface 32. Internally, a concentric breath flow passage 34 extends through the body 26 as readily appreciated from FIG. 4.

Figure 5:
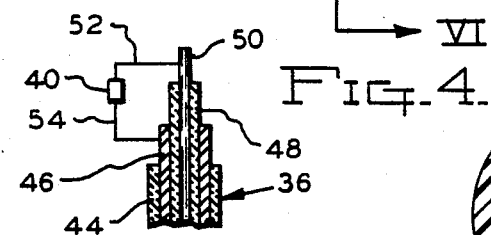
FIG. 5 is an enlarged, diametrical, sectional view of the end of the transducer located within the breathing passage of the transducer.
Figure 6:
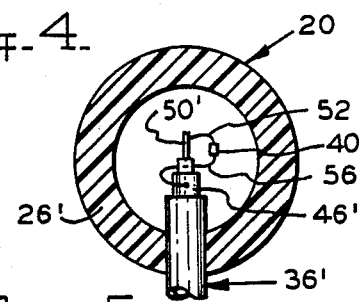
FIG. 6 is an elevational, sectional view as taken along Section VI—VI of FIG. 4 illustrating a modification of the thermobead transistor leads as compared with that shown in FIGS. 4 and 5.

The sensor cable 36 is received within a radial bore in the body 26 intersecting the passage 34, and in FIGS. 4-6 the cable is of the coaxial type, and the inner cable end 38 is located within the passage 34 and is stripped back whereby the terminal wires of the thermobead 40 may be connected to the cable conductors.

The inner diameter of passage 34 will vary in size depending on the size of the animal with which the apparatus is being used. In the commercial embodiment a 0.014 inch diameter thermobead is used of 62K ohm resistance. Such a thermobead is available from Thermometrics of Edison, N.J., Model BR14PB623N. Such a thermobead includes electronic properties for heating itself to approximately 200 degrees Centigrade at its specified operating conditions. The thermobead is sensitive to the surrounding temperature, and heat exchange between the surrounding air and thermobead is substantially instantaneous.

To insure a firm positioning and accurate orientation of the transducer cable 36 within the transducer 20 a tape 42 is wound on the surface 32 in alignment with the radial portion of the cable 38 as will be appreciated from FIG. 4, and the use of the tape 42, in a simplified manner, produces a rugged and dependable assembly between the cable and transducer body 26.

The coaxial cable 36 includes an outer electrical insulating cover 44, an inner concentric conducting sheath 46, a dielectric inner tube 48, and an inner conductor 50 as apparent in FIG. 5. The thermobead lead 52 is soldered, welded or otherwise electrically or mechanically connected to the conductor 50, while the thermobead lead 54 is mechanically and electrically associated with the conductor 46. As will be appreciated from FIGS. 4 and 5, the leads 52 and 54 are long enough to locate the thermobead 40 far enough from the cable end 38 to permit air flowing through passage 34 to freely circulate about all sides of the thermobead to maximize the exchange of heat between the gas being breathed and the thermobead 40.

FIG. 6 illustrates a modification of thermobead lead arrangement, and in this figure components previously described are indicated by primed reference numerals.

To compensate for expansion and/or movement to the cable bending the thermobead lead 56 may be longer than that represented at 54 and "wound about" the inner insulating tube 48 as illustrated. This greater length and configuration of the lead 56 permits dimensional changes due to expansion, contraction or other physical movement without imposing stress upon the thermobead leads.

Figure 7:
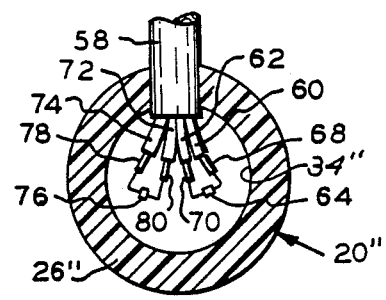
FIG. 7 is a sectional view similar to that of FIG. 6 illustrating another embodiment of the invention wherein a pair of transducers are located within the breathing passage for sensing both breath velocity and body temperature.

Another modification is illustrated in FIG. 7 wherein components identical to those previously described are indicated by double primed reference numerals. In this embodiment a four conductor cable 58 is located within the transducer body 26", and the conductor 58 includes insulated lines 60 and 62 which are connected to the thermobead 64 at conductors 68 and 70. Lines 72 and 74 constitute the pair for supplying the thermobead 76 through conductors 78 and 80. Thus, it will be appreciated that the arrangement of FIG. 7 permits two thermobeads to be located within the transducer air passage 34", and thermobead 64 may be used to sense the breathing characteristics, while thermobead 76 is used for determining the animal body temperature.

Figure 8:
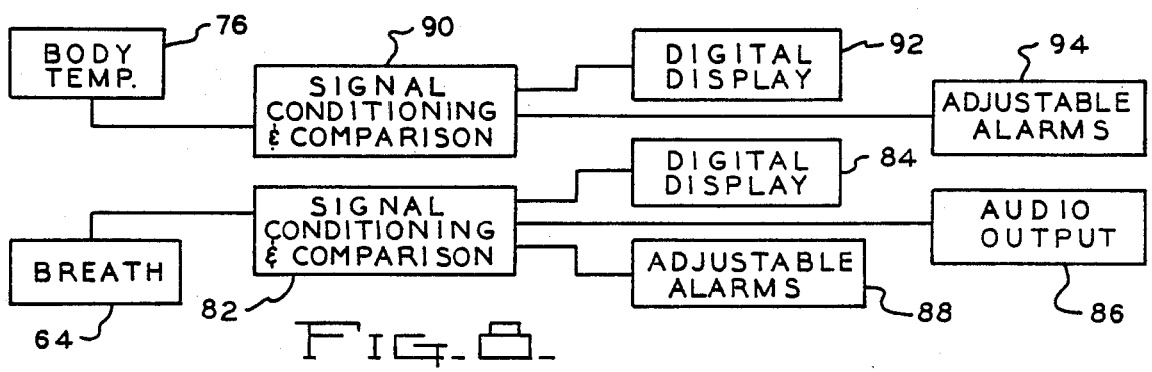
FIG. 8 is a block diagram illustrating a typical arrangement of components used with one or two transducers.

FIG. 8 illustrates typical block circuitry associated with the components of the invention. For instance, the thermobeads 40 or 64 which are to be used to sense breathing characteristics are connected to the signal conditioning and comparison circuitry 82 whose output is used to indicate the animal's breath on a digital or analog display and/or recorder 84 or produce an audio output 86 or operate adjustable alarms 88.

The circuitry 82, which may take any conventional form, produces its output signals dependent upon the electrical characteristics of the associated thermobead 40 or 64, assuming the thermobead 40 is for sensing breathing characteristics. As the animal breathes, the gas flowing through the transducer passage 34 passes over the thermobead 40 or 64 drawing heat away from the thermobead which causes circuitry unbalance modifying the signal being supplied to circuit 82. The heat exchange that takes place between the gas being breathed and the thermobead is only slightly proportional to the temperature of the gas being breathed while being highly sensitive to its velocity as it passes over the thermobead. Thus, the electrical characteristics of the thermobead signal can be interpolated to indicate the volume in liters of gas the animal is inhaling and exhaling with each breath, and may also be interpolated to produce and generate an audio frequency to indicate to the veterinarian the rate and depth of breathing. Such audio signal may be amplified as desired, and the signal may be modified to a neutral or "white" sound so as to be unobtrusive, yet discernible. The duration of the thermobead signal, and the extent of heat transfer that occurs during each breathing cycle, can be interpolated to indicate the volume of gas being breathed in liters per minute, and it is to be appreciated that when analyzing breathing characteristics, either inhalation or exhalation gas flow, or both, can be sensed.

For temperature indicating purposes the thermobead 76, or 40, are connected to signal conditioning and comparison circuit 90 which produces output signals for operating a digital or analog display and recorder 92 and adjustable alarms 94. The circuitry 90 interpolates the signal received from the associated thermobead to indicate the animal body temperature, and, of course, when sensing temperature the breath is only analyzed during exhalation. While some temperature loss may occur during exhaling, the circuitry 90 may be designed to compensate for such temperature loss, and to compensate for the velocity of gas flow past the associated thermobead.

It will be appreciated that the apparatus of the invention meets the aforementioned objects and advantages, and the disclosed apparatus permits the described animal body functions to be accurately monitored and interpolated, and the use of the adjustable alarms permits the veterinarian to be forewarned of the existence of life-threatening situations. A plurality of monitoring systems may be used with a number of animals during recovery, and it is appreciated that various modifications to the inventive concepts may be apparent to those skilled in the art without departing from the spirit and scope of the invention.

We claim:

1. The method of sensing the breathing characteristics of animals comprising the steps of:
    (a) passing the animal's breath through a tube,
    (b) sensing the velocity of the gas the animal is breathing through the tube during a breathing cycle with a heated diode thermobead,
    (c) producing a continuous electrical first signal from said thermobead having a value determined by the velocity of the gas being breathed, and
    (d) producing a continuous second signal from said first signal to permit evaluation of the animal's breathing functions including duration and volume of each breath, said second signal including an audio signal varying in volume, frequency and duration proportional to the velocity and duration of the gas being breathed during each breath simulating a breathing sound.

2. The method of sensing the breathing characteristics of animals as in claim 1 wherein said second signal operates a display and recorder to permanently record the characteristics of the animal's breath during each breath.

3. The method of sensing the breathing and temperature characteristics of animals comprising the steps of:
    (a) passing the animal's breath through a tube,
    (b) separately sensing the temperature and velocity of the gas the animal is breathing through the tube during each breath,
    (c) producing a pair of electrical control signals having values determined by the temperature, velocity and duration of the animal's breath during exhalation,
    (d) producing a first continuous signal from one of said control signals to indicate the velocity and volume of gas being exhaled during each breathing cycle simulating a breathing sound, and
    (e) producing a second signal from the other of said control signals to indicate the body temperature of the animal.

4. Apparatus for sensing the characteristics of the breath of animals comprising, in combination, a tube having a passage conducting the gas being breathed by an animal, a heated diode thermobead within said tube passage sensing the velocity and duration of the gas being breathed during the breathing cycle by sensing the exchange of heat between said thermobead and the gas being breathed and producing an electrical output signal proportional to such velocity and duration, and electrical indicator means receiving said output signal and producing a continuous audible indication of the condition of the animal's breathing functions during the duration of each breath by producing a simulated breathing sound.

* * * * *